US010314932B2

(12) United States Patent
Huang

(10) Patent No.: US 10,314,932 B2
(45) Date of Patent: Jun. 11, 2019

(54) PORTABLE OZONE GENERATOR

(71) Applicant: POG Technologies Inc., St. Albert (CA)

(72) Inventor: CanJun Huang, Shenzhen (CN)

(73) Assignee: 2059492 Alberta Ltd., Edmonton, Alberta (CA)

( * ) Notice: Subject to any disclaimer, the term of this patent is extended or adjusted under 35 U.S.C. 154(b) by 13 days.

(21) Appl. No.: 15/223,519

(22) Filed: Jul. 29, 2016

(65) Prior Publication Data
US 2017/0202993 A1 Jul. 20, 2017

Related U.S. Application Data

(60) Provisional application No. 62/279,666, filed on Jan. 15, 2016, provisional application No. 62/288,323, filed on Jan. 28, 2016.

(51) Int. Cl.
A61L 9/015 (2006.01)
C01B 13/11 (2006.01)
(Continued)

(52) U.S. Cl.
CPC ............ A61L 9/015 (2013.01); A61L 2/14 (2013.01); A61L 2/202 (2013.01); A61L 9/22 (2013.01);
(Continued)

(58) Field of Classification Search
CPC ... A61L 9/015; A61L 2209/212; C01B 13/115
See application file for complete search history.

(56) References Cited

U.S. PATENT DOCUMENTS 5,087,428 A 2/1992 Fletcher et al.
5,316,182 A 5/1994 Lee
(Continued)

FOREIGN PATENT DOCUMENTS

CA 2083967 12/1991
CA 2679102 9/2008
(Continued)

OTHER PUBLICATIONS

Beware of Ozone-generating Indoor "Air Purifiers", California Environmental Protection Agency, published at least as early as Mar. 2006, 7 pages.
(Continued)

Primary Examiner — Kevin Joyner
(74) Attorney, Agent, or Firm — Davis & Bujold PLLC; Michael J. Bujold

(57) ABSTRACT

Portable ozone generators and methods of use. For example, a hand-held portable ozone generator has: a housing defining an air inlet, an air outlet, and an air channel communicating between the air inlet and the air outlet; a battery; an ozone generator configured to output, during operation, ozone into the air channel at a non-zero rate that is equal to or below 50 mg/hour; and a controller connected to send control signals to the ozone generator in response to user input. In other cases, a plank or slab shaped portable ozone generator is disclosed, with an air inlet and an air outlet located in respective opposed face plates. In one case the unit has no defined base, and every face and side wall of the device forms a ground engaging base, and the unit functions properly regardless of what face or side wall the unit contacts the ground or a horizontal ground surface with.

15 Claims, 12 Drawing Sheets

(51) Int. Cl.
*A61L 2/14* (2006.01)
*A61L 2/20* (2006.01)
*A61L 9/22* (2006.01)
*C01B 13/10* (2006.01)

(52) U.S. Cl.
CPC ........... *C01B 13/10* (2013.01); *A61L 2202/16* (2013.01); *A61L 2202/25* (2013.01); *A61L 2209/134* (2013.01); *A61L 2209/212* (2013.01); *C01B 2201/62* (2013.01); *C01B 2201/90* (2013.01)

(56) References Cited

U.S. PATENT DOCUMENTS

| | | |
|---|---|---|
| 5,429,271 A | 7/1995 | Porter |
| 5,457,054 A | 10/1995 | Geisinger |
| 5,514,345 A | 5/1996 | Garbutt |
| 5,525,310 A | 6/1996 | Decker |
| 5,835,840 A | 11/1998 | Goswami |
| 5,911,957 A | 6/1999 | Khatchatrian |
| 5,930,915 A | 8/1999 | Dhaemers |
| 6,074,608 A | 6/2000 | Matz |
| 6,134,806 A | 10/2000 | Dhaemers |
| 6,153,111 A | 11/2000 | Conrad |
| 6,182,671 B1 | 2/2001 | Taylor |
| D457,946 S | 5/2002 | Barnes |
| RE38,231 E | 8/2003 | Fargason |
| 6,630,105 B1 | 10/2003 | O'Neill |
| 6,632,407 B1 | 10/2003 | Lau |
| 6,679,419 B1 | 1/2004 | Sarracino |
| 7,222,634 B2 | 5/2007 | Hess |
| 7,449,053 B2 * | 11/2008 | Hallam .................. A61L 9/015 95/58 |
| 7,939,015 B1 | 5/2011 | Elrod |
| 8,066,939 B2 | 11/2011 | Elrod |
| 8,187,533 B2 | 5/2012 | Elrod |
| 8,257,648 B2 | 9/2012 | Elrod |
| 8,329,096 B2 | 12/2012 | Elrod |
| 8,404,180 B1 | 3/2013 | Elrod |
| D687,531 S | 8/2013 | Swagel |
| 8,557,177 B1 | 10/2013 | Elrod |
| 8,663,553 B2 | 3/2014 | Elrod |
| 2001/0032544 A1 * | 10/2001 | Taylor .................. A01K 1/0107 96/19 |
| 2002/0094298 A1 | 7/2002 | Monagan |
| 2003/0159200 A1 | 8/2003 | Elrod |
| 2004/0047775 A1 | 3/2004 | Lau |
| 2004/0221396 A1 | 11/2004 | Johnson |
| 2004/0222165 A1 | 11/2004 | Michocki |
| 2005/0147545 A1 * | 7/2005 | Lau ......... B01D 53/32 422/186.04 |
| 2005/0186108 A1 | 8/2005 | Fields |
| 2006/0151896 A1 | 7/2006 | Wang |
| 2006/0266221 A1 | 11/2006 | Fink |
| 2007/0166186 A1 | 7/2007 | Stec |
| 2007/0212253 A1 | 9/2007 | Elrod |
| 2008/0036594 A1 | 2/2008 | Kates |
| 2008/0118411 A1 * | 5/2008 | D'Arinzo ................. A61L 2/202 422/186.09 |
| 2008/0168790 A1 * | 7/2008 | Hurlebaus ............... A61L 9/205 62/331 |
| 2010/0289655 A1 | 11/2010 | Elrod |
| 2012/0134876 A1 | 5/2012 | Elrod |
| 2012/0244036 A1 * | 9/2012 | Benedek .................. A61L 9/015 422/4 |
| 2013/0125944 A1 | 5/2013 | Elrod |
| 2014/0178255 A1 | 6/2014 | Elrod |
| 2017/0165387 A1 * | 6/2017 | Robert ....................... A61L 2/14 |

FOREIGN PATENT DOCUMENTS

| | | |
|---|---|---|
| CA | 2799281 | 11/2011 |
| CA | 2855707 | 5/2013 |
| CN | 2597512 | 1/2004 |
| CN | 104001397 A * | 8/2014 |
| EP | 1057923 | 12/2000 |
| JP | H08168363 A | 7/1996 |
| JP | 2002345937 A | 12/2002 |
| JP | 2003024426 A | 1/2003 |
| WO | 2005077425 A1 | 8/2005 |
| WO | 2008064236 | 5/2008 |
| WO | 2010065103 | 6/2010 |
| WO | 2011005297 | 1/2011 |
| WO | 2013078282 | 5/2013 |

OTHER PUBLICATIONS

Britigan, Quantification of Ozone Levels in Indoor Environments Generated by Ionization and Ozonolysis Air Purifiers, J. Atr. & Waste Manage. Assoc., May 2006, 601-610, 56.

Wayback machine archive of Ameripure Technologies Biozone TravelAire 250 Air Purifier, URL=http://web.archive.org/web/20060825212240/http://www.purifymyair.com/biozonetravelaire250airpurifier.htm, published at least as early as Aug. 25, 2006, 3 pages.

Wayback machine archive of Game Finder Bomms Terminator, URL=https://web.archive.org/web/20060206054059/http://gamefinder.com/bommsterminator.aspx, published at least as early as Feb. 6, 2006, 3 pages.

DC-12 Home and Auto Ozone Generator on Amazon, URL=https://www.amazon.com/DC-12-Generator-Cleaner-Deodorizer-Purifier/dp/B00l12L2BK, believed to be available since at least as early as Jan. 15, 2016, 8 pages.

Wayback machine archive of Jenesco website ozone generator page, URL=https://web.archive.org/web/20070221024552/http://www.jenesco.com/ozonegenerator.html, published at least as early as Feb. 21, 2007, 4 pages.

Wayback machine archive of Jenesco website home page, URL= http://web.archive.org/web/20070225182507/http://www.jenesco.com/, published at least as early as Feb. 25, 2007, 6 pages.

Wayback machine archive of Jenesco website DC-12 page, URL= http://web.archive.org/web/20070216022350/http://www.jenesco.com/cart/html/Products/OzoneGenerators/DC1210.html, published at least as early as Feb. 16, 2007, 2 pages.

Wayback machine archive of Jenesco website PRO-4 page, URL= http://web.archive.org/web/20060322082451/http://www.jenesco.com/shop/product_info.php/cPath/32/products_id/212, published at least as early as Mar. 22, 2006, 2 pages.

Alibaba—Water purifier, URL=http://www.alibaba.com/productdetail/Charminghotsaleminiozonewater_60241000671.html?app=affiliate&s=p&spm=a2700.7906341.35.1.nUkADC, believed to have been available since at least as early as Jan. 15, 2016, 9 pages.

Wayback machine archive of Jenesco website FM-12 page, URL= http://web.archive.org/web/20060704025706/http://www.jenesco.com/ozonegenerator/index.html, published at least as early as Jul. 4, 2006, 2 pages.

Wayback machine archive of Game Finder home page, URL=https://web.archive.org/web/20061213021015/http://www.gamefinder.com/, published at least as early as Dec. 13, 2006, 2 pages.

Shenzhen Trume Technology Alibaba—Necklace Ozone Sterilizer, URL=http://trumeozone.en.alibaba.com/product/60132132507800521463/Mini_necklace_air_purifier_personal_air_ionizer.html, believed to have been available since at least as early as Jan. 15, 2016, 9 pages.

Shenzhen Trume Technology Alibaba—N201B, URL=http://trumeozone.en.alibaba.com/product/1153165970800530121/Car_airFreshener_with_ionizer_and_ozonizer_and_perfume.html, believed to have been available since at least as early as Jan. 15, 2016, 5 pages.

Shenzhen Trume Technology Alibaba—N206, URL=http://trumeozone.en.alibaba.com/product/60074347014800252730/Wall_mounted_ozone_air_purifier_ozon_generator_electronic_ozonizer_aire.html, believed to have been available since at least as early as Jan. 15, 2016, 12 pages.

Shenzhen Trume Technology Alibaba—N231, URL=http://trumeozone.en.alibaba.com/product/602486239140/500mg_h_mini_ozone_

(56) References Cited

OTHER PUBLICATIONS generator_small_air_ozonizer.html, believed to have been available since at least as early as Jan, 15, 2016, 8 pages.
Shenzhen Trume Technology Alibaba—N318, URL=http://trumeozone.en.alibaba.com/product/1144983029219203259/tap_Ozone_Generator_with_Timer_and_LCD_display_and_500mg_h.html, believed to have been available since at least as early as Jan. 15, 2016, 10 pages.
Shenzhen Trume Technology Alibaba—N328, URL=http://trumeozone.en.alibaba.com/product/60306594079800526168/Fridge_Ozonator_to_keep_fruit_and_vegetable_fresh_O3.html, believed to have been available since at least as early as Jan. 15, 2016, 11 pages.
Shenzhen Trume Technology Alibaba—N328 alternate page, URL=http://trumeozone.en.alibaba.com/product/1215120319219098319/2015_new_mini_portable_Fridge_Ozonizer_with_ozone_density_5mg_h.html, believed to have been available since at least as early as Jan. 15, 2016, 7 pages.
Shenzhen Trume Technology Alibaba—N329, URL=http://trumeozone.en.alibaba.com/product/60312055369800526169/Ozone_20mg_h_Battery_Power_Source_and_Ozone_Generator_Type_Fridge_Purifier.html, believed to have been available since at least as early as Jan. 15, 2016, 10 pages.
Alibaba—N339 plug in ozone generator, URL=http://www.alibaba.com/productdetail/NanbaiN339pluginozonegenerator_60269097987.html?app=affiliate&spm=a2700.7906341.35.1.nUkADC, believed to have been available since at least as early as Jan. 15, 2016, 11 pages.
Shenzhen Trume Technology Alibaba—N366, URL=http://trumeozone.en.alibaba.com/product/60307243486800530123/Electrical_Power_Source_and_Portable_Installation_car_air_purifier.html, believed to have been available since at least as early as Jan. 15, 2016, 11 pages.
Shenzhen Trume Technology Alibaba—N381, URL=http://trumeozone.en.alibaba.com/product/1971941095222743424/ESP_mini_3w_Beauty_Air_Purifier_Cleaner_Fresher_Deodorizer_Sterilizer_Sterilizer.html, believed to have been available since at least as early as Jan. 15, 2016, 5 pages.
Alibaba—N812 portable ozone generator, URL=http://www.alibaba.com/productdetail/N812PortableOzoneAirPurifierOzone_60296833320.html, believed to have been available since at least as early as Jan. 15, 2016, 10 pages.
Shenzhen Trume Technology Alibaba—N888, URL=http://trumeozone.en.alibaba.com/product/60093497015219977674/Portabel_Power_Bank.html, believed to be available at least as early as Jan. 15, 2016, 3 pages.
Shenzhen Trume Technology Alibaba—N1668, URL=https://trumeozone.en.alibaba.com/product/60300126323-800521688/DC12V_Portable_Installation_and_CB_CE_EMC_EMF_RoHS_UL_UR_Certification_ozonizer_air_purifier_ozonizer.html, believed to have been available since at least as early as Jan. 15, 2016, 14 pages.
Scent Crusher Ozone Gear Bag web page, URL=http://scentcrusher.com/gearbag/, accessed on Jan. 13, 2016, 2 pages.
Wayback machine archive of Game Finder Terminator 800 web page, URL=hhttps://web.archive.org/web/20060206053900/http://gamefinder.com/terminator800.aspx, published at least as early as Feb. 6, 2006, 2 pages.
Shenzhen Trume Technology Product List, believed to have been available since at least as early as Jan. 15, 2016, 3 pages.
Shenzhen Trume Technology Alibaba—N1668, URL=https://www.alibaba.com/product-detail/negative-ion-ioncare-usb-ionizer-Air_60300898070.html, believed to have been available since at least as early as Jan. 15, 2016, 10 pages.

\* cited by examiner

PORTABLE OZONE GENERATOR

TECHNICAL FIELD

This document relates to portable ozone generators and methods of use.

BACKGROUND

Battery and wall plug operated ozone generators are used to deodorize refrigerators, rooms, water, clothing, and other items.

SUMMARY

Portable ozone generators are disclosed, for example hand-held units. For example, a hand-held portable ozone generator is disclosed comprising: a housing defining an air inlet, an air outlet, and an air channel communicating between the air inlet and the air outlet; a battery; an ozone generator configured to output, during operation, ozone into the air channel at a non-zero rate, for example a rate that is equal to or below 50 mg/hour; and a controller connected to send control signals to the ozone generator in response to user input. In other cases, a plank or slab shaped portable ozone generator is disclosed, with an air inlet and an air outlet located in respective opposed face plates. In one case the unit has no defined base, and every face and side wall of the device forms a ground engaging base, and the unit functions properly regardless of what face or side wall the unit contacts the ground or a horizontal ground surface with.

Methods of use of portable ozone generators are also disclosed. In various embodiments, there may be included any one or more of the following features: The ozone generator is configured to output ozone at a non-zero rate that is at least 20 mg/hour and at most 50 mg/hour. The housing comprises an encircling wall and first and second face plates opposing one another. External surfaces of the housing form a plank shape. The air inlet is defined through the first face plate, and the air outlet is defined through the second face plate. The air inlet, air outlet, and air channel align to form a straight air flow path into and out of the housing. A fan is mounted across the air channel such that an axis of blade rotation of the fan is parallel with an air channel axis. The encircling wall comprises one or more lateral air inlets communicating with the air channel. The first face plate is shaped to permit air flow into the air inlet when the first face plate is resting on a planar surface. The second face plate is shaped to permit air flow into the air outlet when the second face plate is resting on the planar surface. The air channel has a generally cylindrical cross-sectional shape from the air inlet to the air outlet. The encircling wall defines a support structure laterally extended between opposed interior facing surfaces of the encircling wall. The support structure is located part way between the first and second face plates. The support structure mounts the battery, ozone generator, and controller. The support structure comprises a partition plate that defines part of the air channel and mounts a corona discharge electrode, of the ozone generator, across the air channel. Plural reinforcing members are extended internally between the first and second face plates. The plural reinforcing members comprise posts that pass through apertures defined in the support structure. The battery forms a reinforcing member extended between the first and second face plates. One or more control buttons are accessible from an exterior of the housing. The controller comprises a timer. The controller is programmed to operate the ozone generator for a selected period of time in response to control signals to the controller from the one or more control buttons. The battery is a permanent internal rechargeable battery. A power output, for example a Universal Serial Bus (USB) port, is connected to the battery and accessible from an exterior of the housing. External edges and external corners of the housing are beveled, curved, or beveled and curved. The controller is used to instruct the ozone generator to enter an ozone production mode. Deodorizing one or more items by placing the hand-held portable ozone generator, while in the ozone production mode, in a bag along with the one or more items. The handheld ozone generator deodorizes clothing such as sports or hunting clothes. The handheld ozone generator deodorizes equipment such as sports or hunting equipment. The handheld ozone generator deodorizes scent resistant clothing. The scent resistant clothing comprises activated carbon. The handheld ozone generator deodorizes the interior of a vehicle. The vehicle is a recreation vehicle. The handheld ozone generator deodorizes a user's body or clothing by contacting the user's skin or clothing directly with the hand-held ozone generator. The hand-held ozone generator deodorizes pet odor from an enclosed area. Deodorizing includes sanitizing, for example to kill one or both bacteria or fungus.

These and other aspects of the device and method are set out in the claims, which are incorporated here by reference.

BRIEF DESCRIPTION OF THE FIGURES

Embodiments will now be described with reference to the figures, in which like reference characters denote like elements, by way of example, and in which.

DETAILED DESCRIPTION

Immaterial modifications may be made to the embodiments described here without departing from what is covered by the claims.

Figure 1:
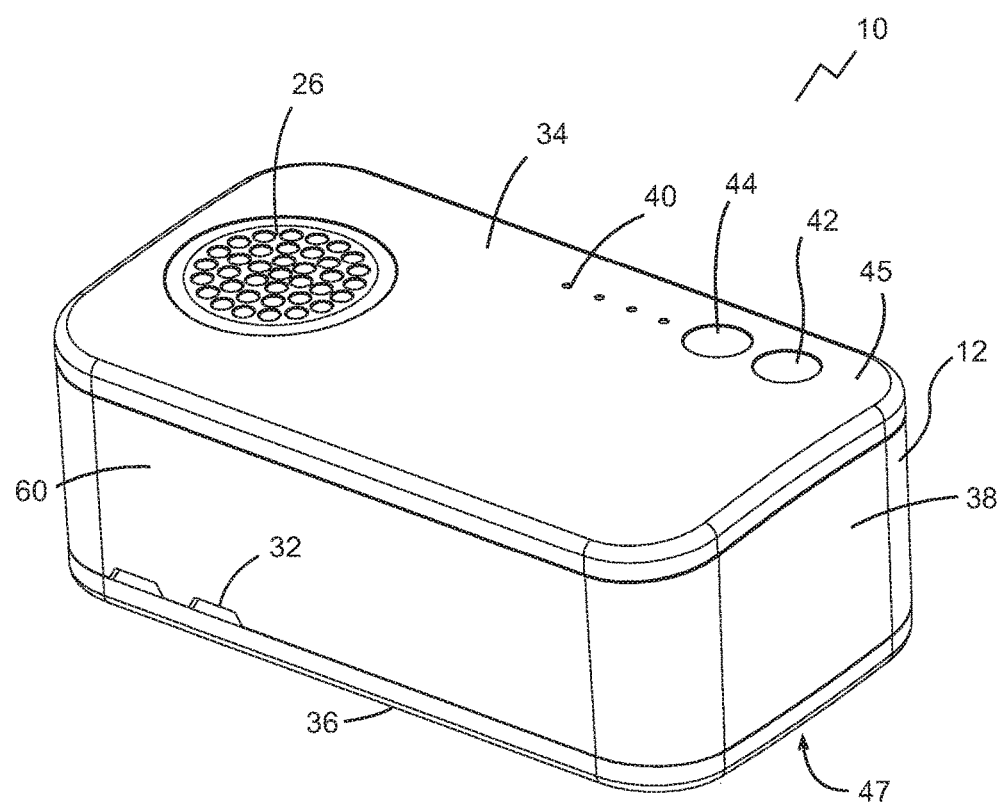
FIG. 1 is a side perspective view of a portable ozone generator.
Figure 8:
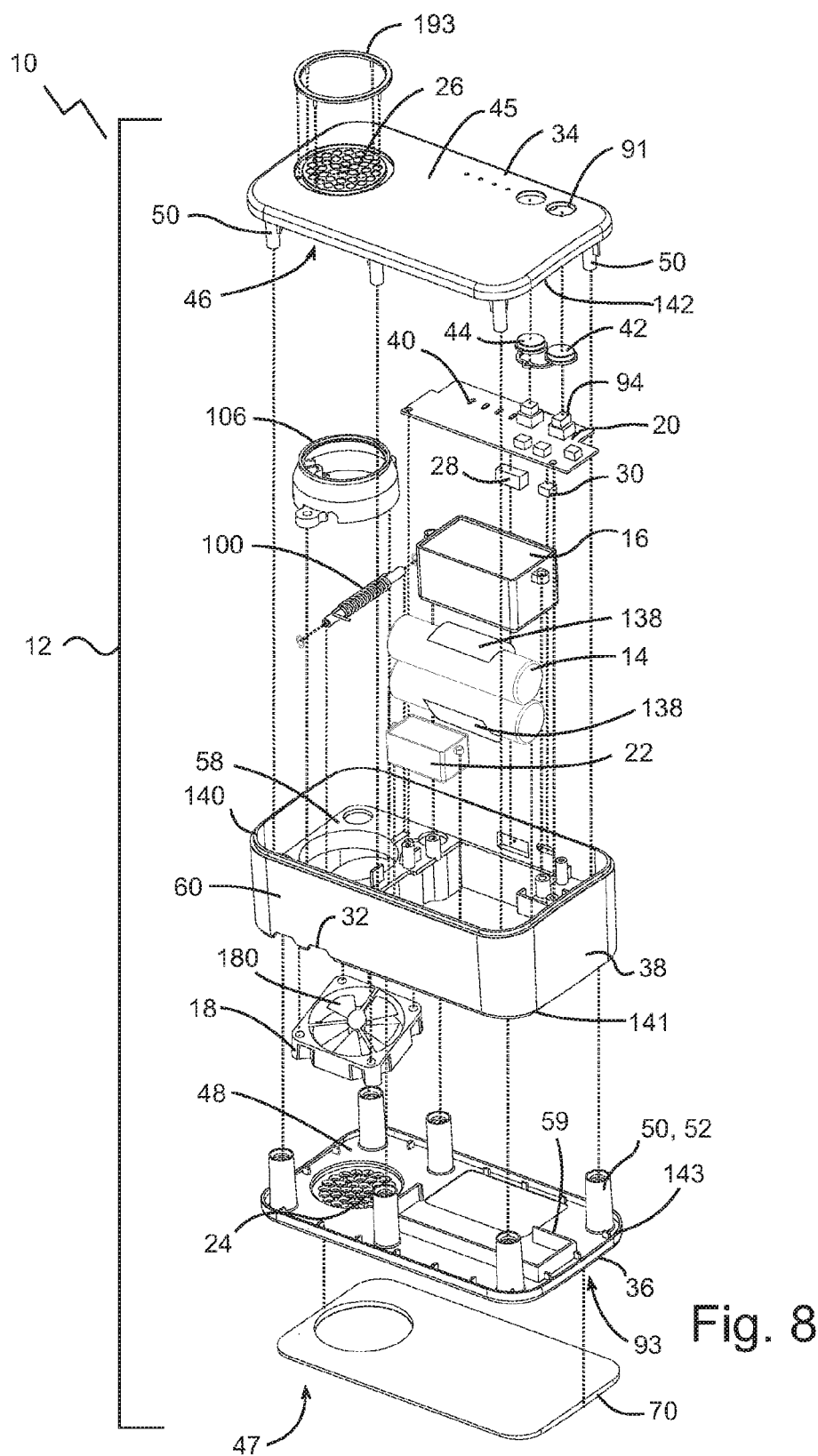
FIG. 8 is an exploded perspective view of the portable ozone generator depicted in FIG. 1.
Figure 11:
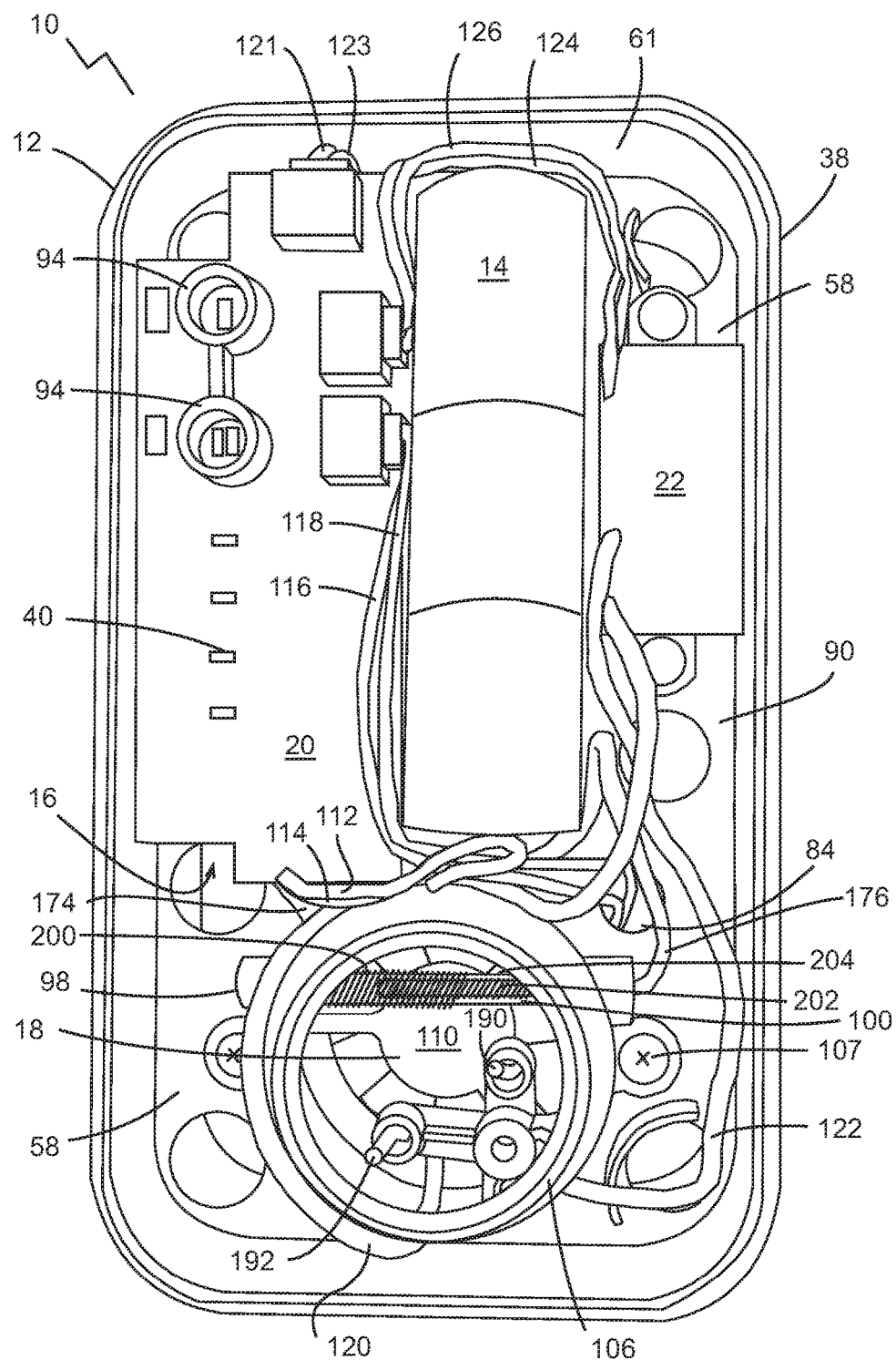
FIG. 11 is a top plan view of the encircling wall and support structure, with mounted components, of the portable ozone generator depicted in FIG. 1.
Figure 17:
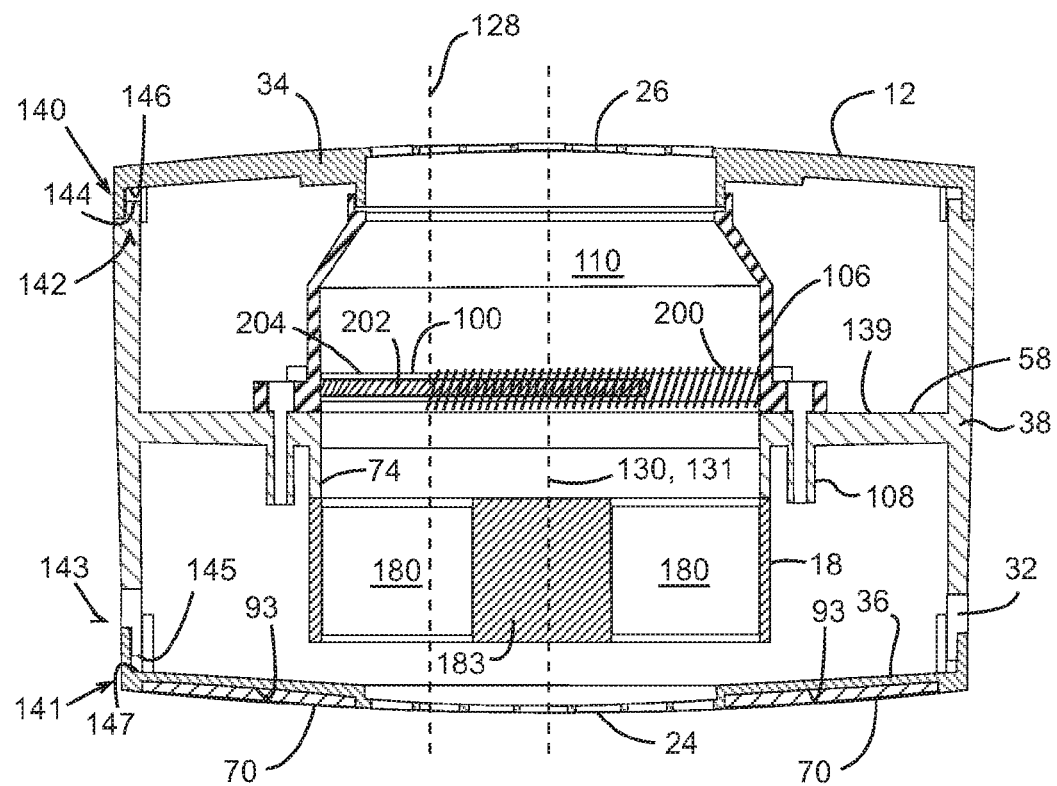
FIG. 17 is a section view taken along the 17-17 lines in FIG. 2 and illustrating an air channel through the device.

Referring to FIG. 1, a portable ozone generator 10 is shown. Referring to FIG. 8, portable ozone generator 10, such as a hand-held unit as shown, comprises a housing 12, a battery 14, an ozone generator 16, and a controller, such as circuit board 20. Referring to FIG. 17, housing 12 may define an air outlet 26, an air inlet 24, and an air channel 110 communicating between the air inlet 24 and the air outlet 26. The ozone generator 16 may be configured to output ozone, for example using corona discharge tube 100, into the air channel 110 at a non-zero rate, which may be equal to or below 50 mg/hour. Referring to FIG. 11, the circuit board 20 is connected to send control signals to the ozone generator 16 in response to user input, for example from one or more buttons 42, 44. In one case the portable ozone generator 10 comprises a fan 18. In one case the generator 10 comprises an ioniser 22.

Figure 3:
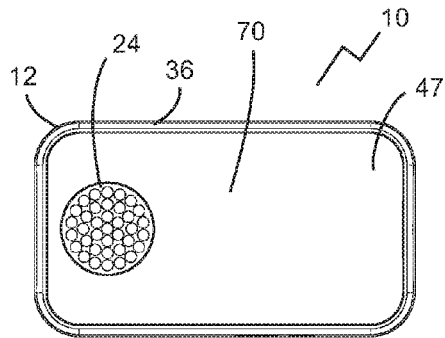
FIG. 3 is a bottom plan view of the portable ozone generator depicted in FIG. 1.
Figure 4:
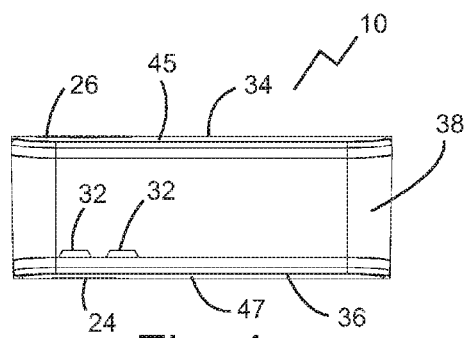
FIG. 4 is a first side elevation view of the portable ozone generator depicted in FIG. 1
Figure 5:
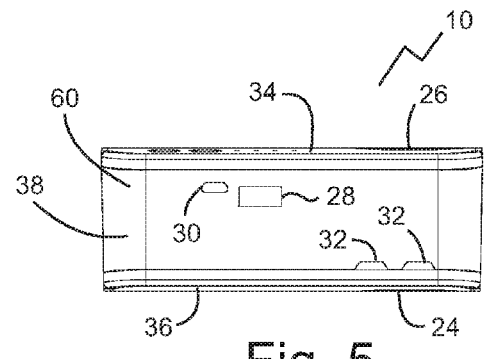
FIG. 5 is a second side elevation view of the portable ozone generator depicted in FIG. 1.
Figure 6:
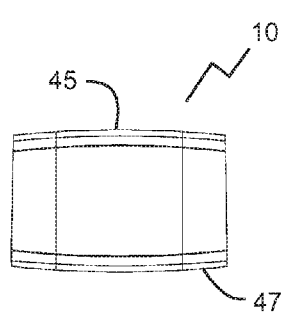
FIG. 6 is a front end elevation view of the portable ozone generator depicted in FIG. 1.

Referring to FIGS. 1, 4 and 5, housing 12 may comprise an encircling wall 38 and first and second face plates 36 and 34 opposing one another. Referring to FIG. 3 housing 12 may comprise cover plate 70 as part of one of the face plates, in this case plate 36. Referring to FIG. 8, face plates 34 and 36 may comprise exterior facing surfaces 45 and 47, and interior facing surfaces 46 and 48, respectively. First face plate 36 may define air inlet 24 and second face plate 34 may define air outlet 26. The terms inlet and outlet merely reflect the direction of flow in the depicted embodiment but flow may be reversed so that air outlet 26 functions as air inlet 24 and vice versa.

In one embodiment, exterior facing surfaces 45, 47 and exterior facing surface 60 of encircling wall 38, collectively form a plank shape. A plank or slab shape refers to a shape where the encircling wall defines a separation distance between the plates, the separation being relatively thin compared to the maximum or local maximum lateral dimensions of the plates, such as the length and width dimensions in the case of rectangular face plates. A plank may also refer to a relatively thin, long flat item or sheet, and in some cases a thin square or rectangular sheet. Referring to FIG. 1, some or all of the external edges and corners of the external surfaces of the housing 12 may be rounded or beveled for ease of handling. A plank may also include a rectangular box or rectangular cuboid, and other terms such as a slate, sheet, bar, tablet, and cell phone, may be used to describe the shape of the housing 12. Face plates 34 and 36 are shown as rectangular, but may have non-rectangular shapes such as circular, oval, polygonal, or other shapes. The rectangular plank shape shown has a low profile, and fits easily within pockets and bags.

Figure 2:
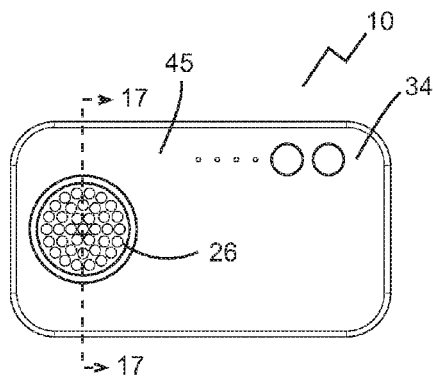
FIG. 2 is a top plan view of the portable ozone generator depicted in FIG. 1.
Figure 7:
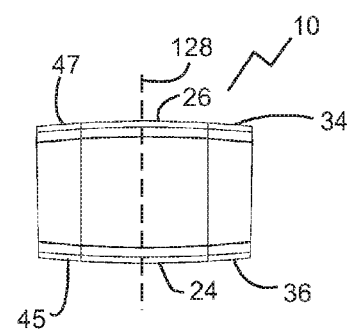
FIG. 7 is a rear end elevation view of another side of the portable ozone generator depicted in FIG. 1.
Figure 14:
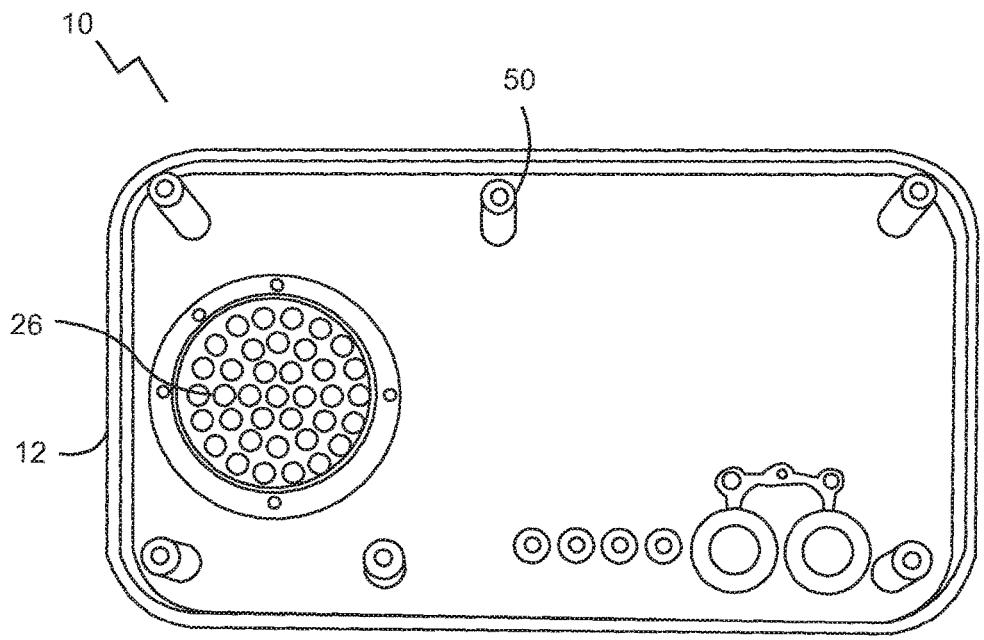
FIG. 14 is a bottom plan view of a top face plate of the portable ozone generator depicted in FIG. 1.
Figure 15:
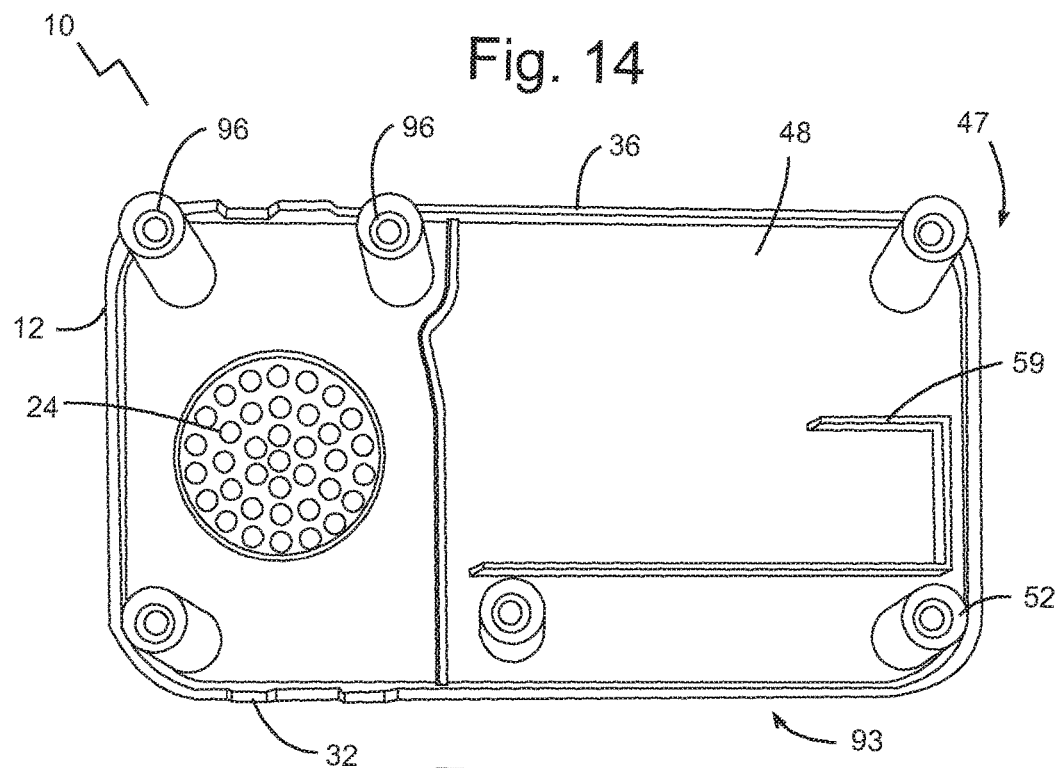
FIG. 15 is a top plan view of a base face plate of the portable ozone generator depicted in FIG. 1.
Figure 19:
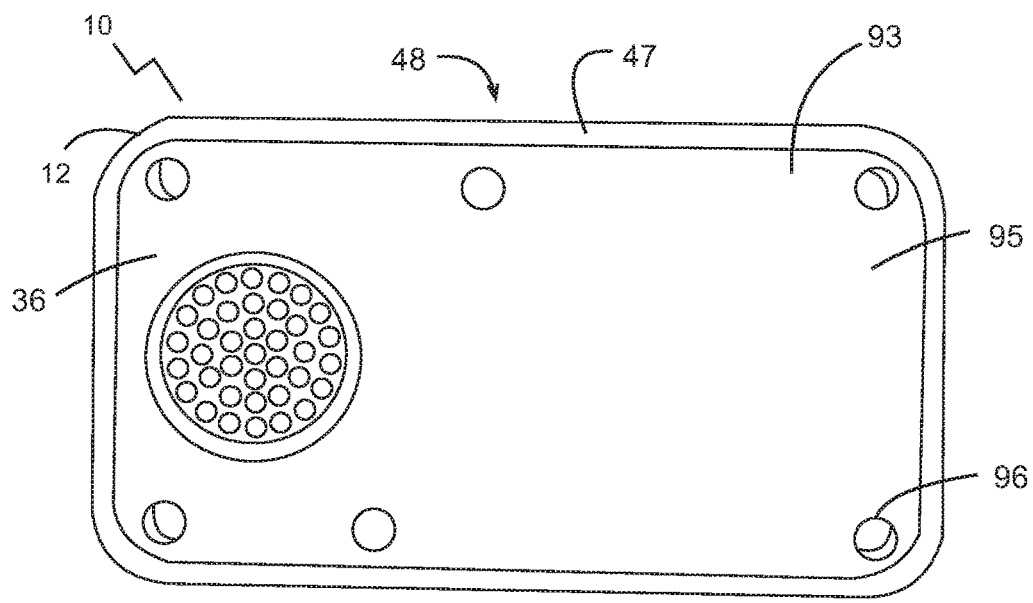
FIG. 19 is a bottom plan view of the base face plate of the portable ozone generator depicted in FIG. 1, with the cover plate removed.

Referring to FIGS. 3, 15 and 19, face plate 36 may comprise exterior facing surface 47 and interior facing surface 48. Referring to FIGS. 2 and 14, second face plate 34 is depicted and may comprise an exterior facing surface 45, an interior facing surface 46 (FIG. 14). Referring to FIG. 7, exterior facing surfaces 47 and 45 may each define a non-linear outer profile in cross-section, for example a cross-section taken along the plane of the page of FIG. 7, in one case parallel to the air channel axis 130. An example non-linear outer profile is a convex curve, to permit air flow into the air ports or inlet/outlets 24 or 26 when the respective face plate 36 or 34 is resting on a planar surface. Other raised or grooved profiles may be used, in order to ensure that part of the air inlet 24 or outlet 26 forms a lateral port that is unblocked when the respective surface 47 or 45 rests upon a planar horizontal surface. Referring to FIGS. 2 and 3, the air inlet 24 and outlet 26 may each be a screen or mesh or other suitable configuration structured to permit free passage of fluid, for example air, ozone or ionized particles. Air inlet 24 may be circular, square or have another suitable shape.

Figure 18:
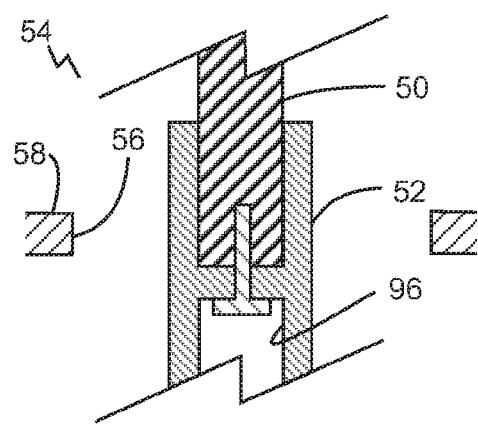
FIG. 18 is a section view of a post-post connection.

Referring to FIG. 8, housing 12 may comprise a plurality of reinforcing members, such as pegs or posts 50, extending internally between the first and second face plates 36 and 34, respectively. In one embodiment, posts 50 extend from interior face 46 to connect, for example nest, with respective opposing posts 52 extended from interior face 48. In one case, battery 14 may form a reinforcing member extended between the first and second face plates, 36 and 34, respectively. One or more shock absorption devices, such as foam pads 138 may be positioned between the battery 14 and the plates 36, 34. In another embodiment (not pictured), posts 50 or 52 may extend from the interior facing surface of one face plate to the other face plate. Referring to FIG. 18, each pair of posts 50 and 52 may form a column 54 when post 50 is nested with its respective, opposing post 52, and each post 50 may be secured by a suitable fastening mechanism such as a screw and thread. Referring to FIG. 8, opposing post 52 may extend from the interior surface 48 of the opposing face plate 36. Columns 54 provide structural integrity for housing 12 and secure face plates 34 and 36 together. The orientation and location of the plurality of posts 50, 52 can be modified from the arrangement shown. Also, in other cases posts 52 may nest within posts 50.

Referring to FIGS. 8 and 17, first face plate 36 may be shaped to accommodate cover plate 70. For example, first face plate 36 may define a groove 93 into which cover plate 70 fits. Referring to FIG. 19, a base surface 95 of groove 93 may define access openings 96 that extend through, for example coaxial with, posts 52 (FIG. 8) and that each receive a fastener such as a screw within posts 52 to secure posts 52 and 50 together as previously discussed (FIG. 18).

Referring to FIGS. 8 and 17, encircling wall 38 may connect to face plates 34, 36 by a suitable mechanism such as interlocking teeth. Referring to FIG. 17, for example, a first rim 140 defined by encircling wall 38 is structured to interlock with a corresponding interior rim 142 of face plate 34, for example if a tongue 144 of wall 38 fits within a corresponding groove 146 of face plate 34. A second rim 141 defined by encircling wall 38 may be structured to interlock with a corresponding interior rim 143 of face plate 36, for example if a tongue 145 of wall 38 fits within a corresponding groove 147 of face plate 36.

Figure 16:
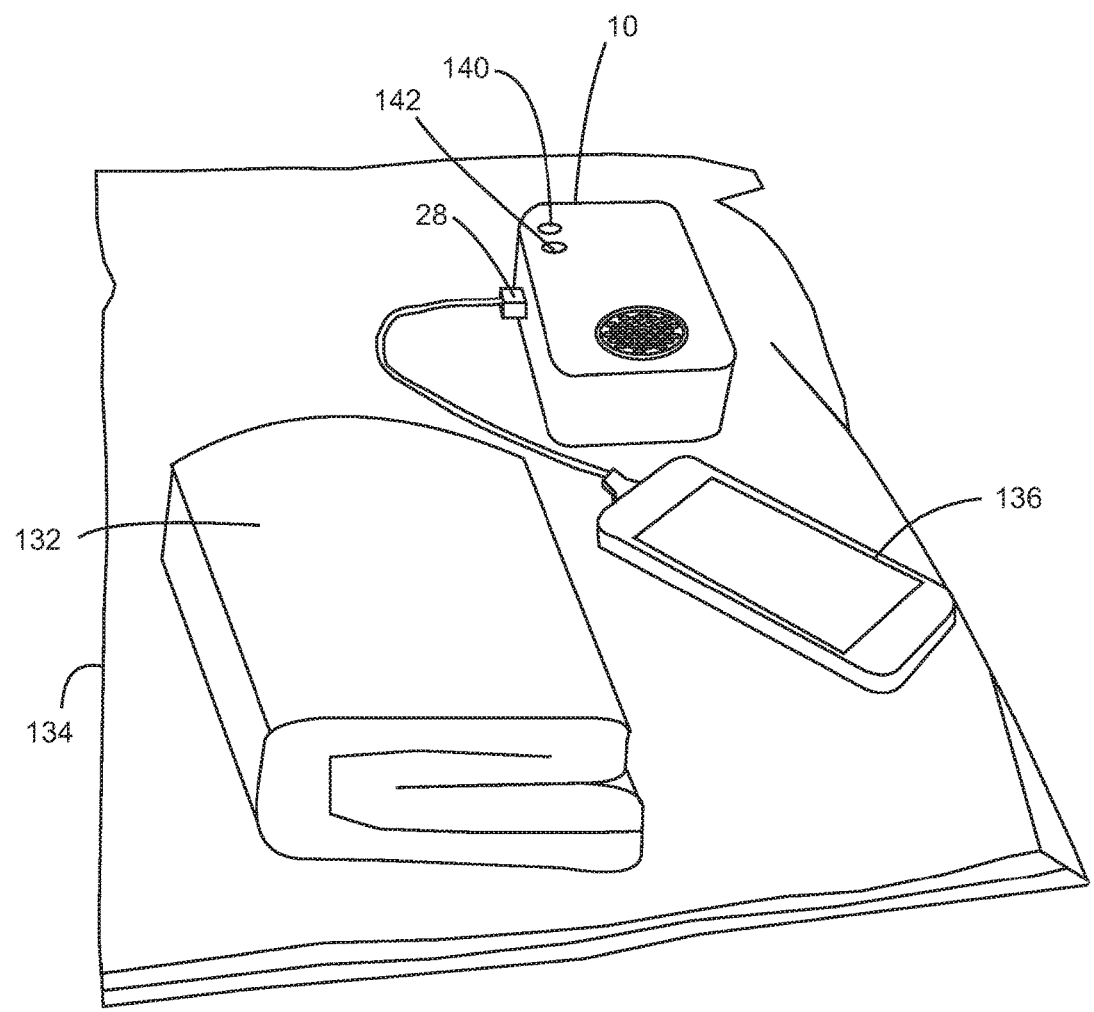
FIG. 16 is a perspective view of a portable ozone generator in use within a bag, deodorizing a towel and charging a cell phone.

Referring to FIG. 5, housing 12, for example encircling wall 38, may also define openings for a power output, such as a USB power outlet 28, connected to battery 14 and accessible from exterior facing surface 60. In one case, one or both of AC and DC power may be outputted. Referring to FIG. 16, such a configuration provides power through the USB port and enables the use of ozone generator 10 as a power bank for USB-powered devices, such as a cell phone 136. Encircling wall 38 may also define openings for a power inlet 30 connected to battery 14 and accessible for exterior surface 60, for example to permit charging of the battery 14 using an adapter plugged into a wall outlet.

Figure 9:
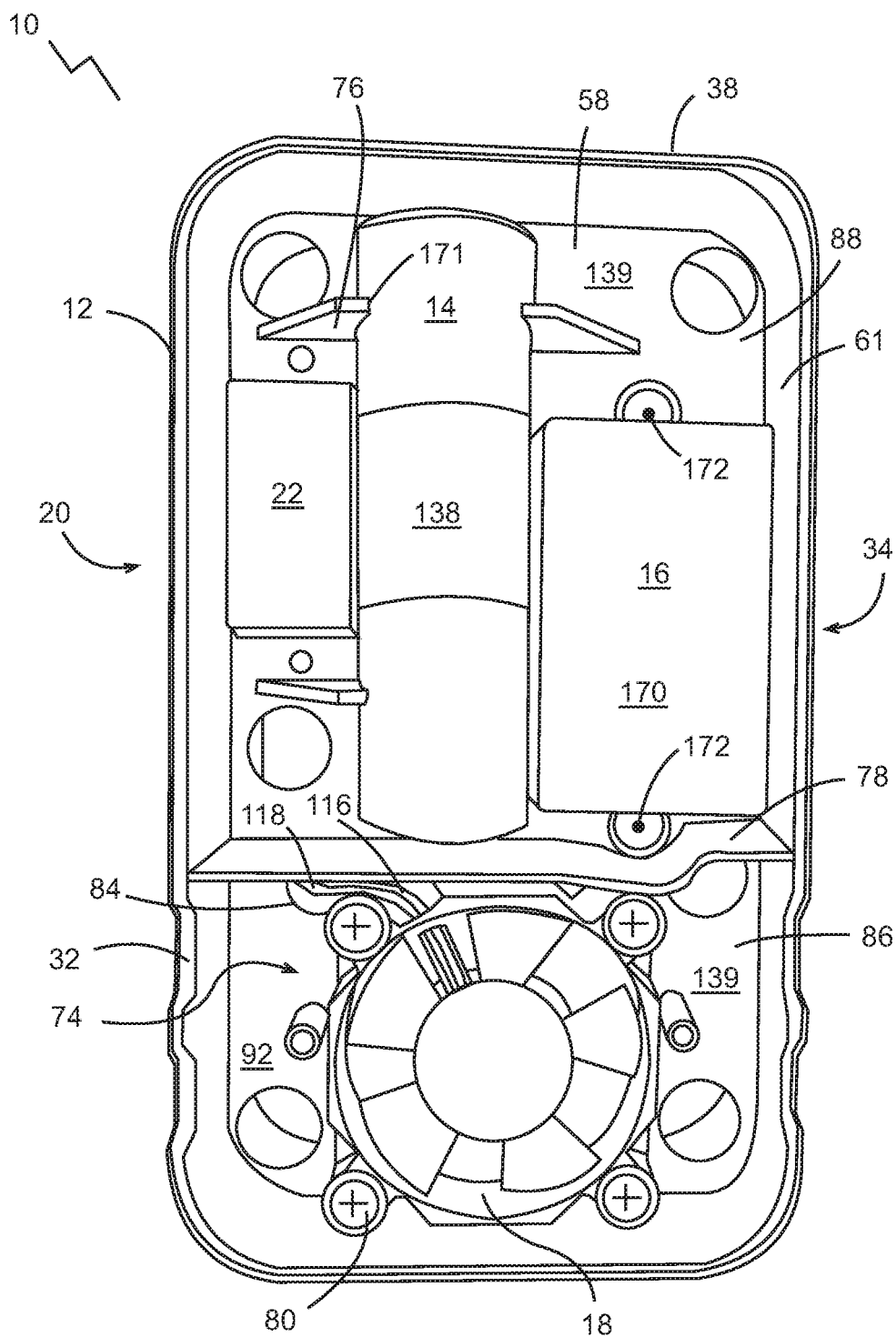
FIG. 9 is a bottom plan view of the encircling wall and support structure with mounted components, of the portable ozone generator depicted in FIG. 1.
Figure 10:
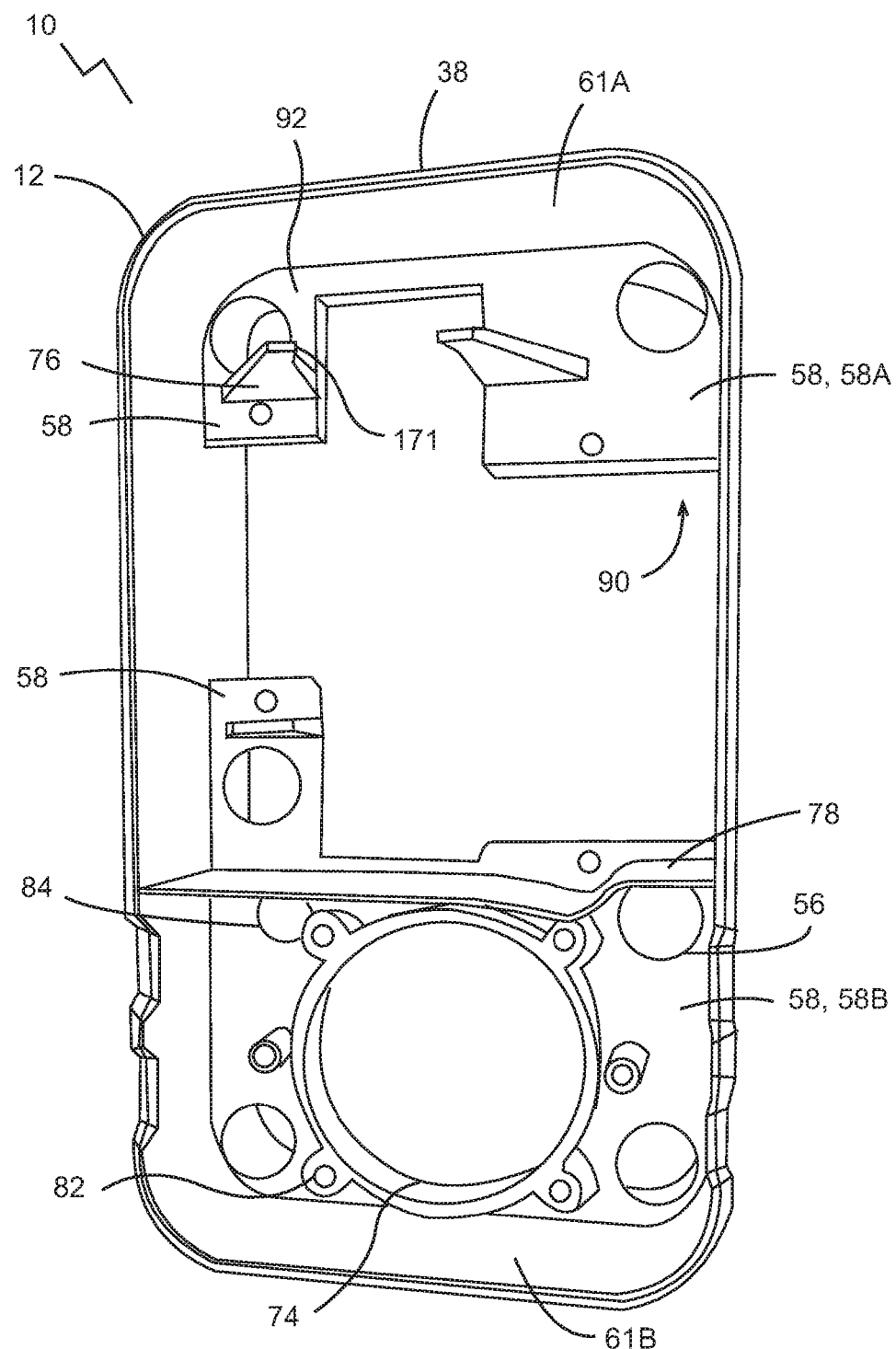
FIG. 10 is a bottom plan view of the encircling wall and support structure, without components mounted, of the portable ozone generator depicted in FIG. 1.

Referring to FIGS. 9-12, perimeter side wall 38 may comprise a support structure 58, such as one or more partition plates 139 (FIG. 9). Referring to FIG. 10, support structure 58 may be laterally extended between opposed interior facing surfaces, such as surface 61A and 61B, of the encircling wall 38. Referring to FIG. 8, support structure 58 may be located part way between the first and second face plates 36 and 34. Referring to FIG. 15, interior facing surface 48 may define supports, such as fins 59, extending out of surface 48 and may be shaped to accommodate or form part of a compartment for battery 14 (not pictured). Referring to FIGS. 9 and 10, in one embodiment, reinforcing members may include fins 76 that extend from support structure 58 toward and in the example shown into contact with, one or more of the face plates 34 or 36, for example to contact fins 59 (FIG. 15). Fins 76 may be shaped, for example hooked at tips 171, to retain battery 14. Referring to FIGS. 9 and 11, component support structure 58 may mount one or more of the battery 14, ozone generator 16, and circuit board 20. Referring to FIG. 10, support structure 58 may thus be configured such that, under external force applied to housing 12, for example a compression force across plates 34, 36, such force is transferred to and withstood by reinforcing members such as posts 50, 52, and fins 76, and diverted away, at least in part, from sensitive internal components. Where the battery 14 may act as a reinforcing member between the plates 34, 36, pads 138 may compress under initial loading to permit limited inward flexing of plates 34, 36 and prevent significant load bearing through battery 14 until the pads 138 are fully depressed. Referring to FIG. 7, as shown, plates 34 and 36 may each have a slight outward curvature that strengthens and rigidifies both plates 34 and 36 against compressive forces.

Figure 12:
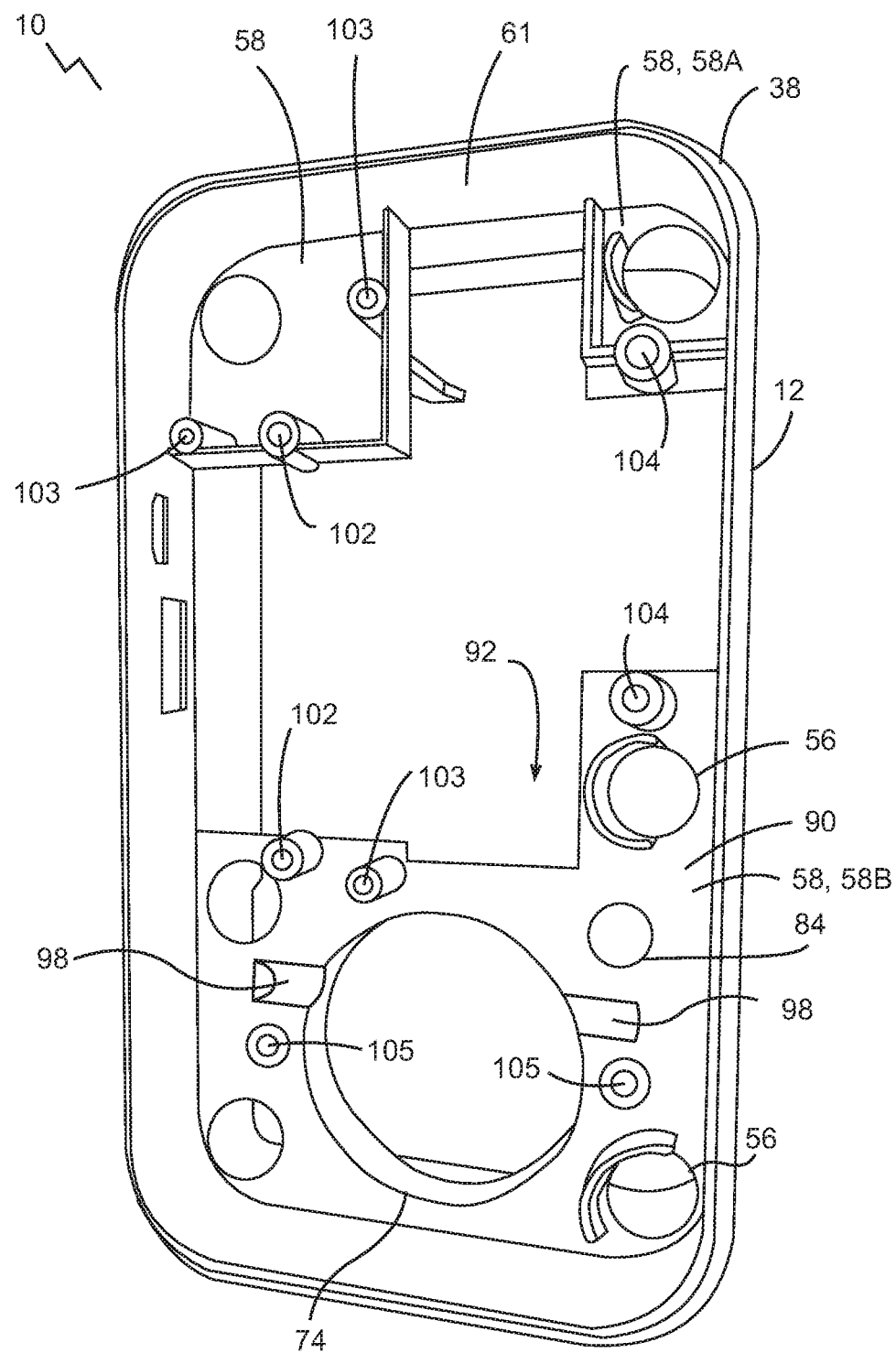
FIG. 12 is a top plan view of the encircling wall and support structure, without components mounted, of the portable ozone generator depicted in FIG. 1.
Figure 13:
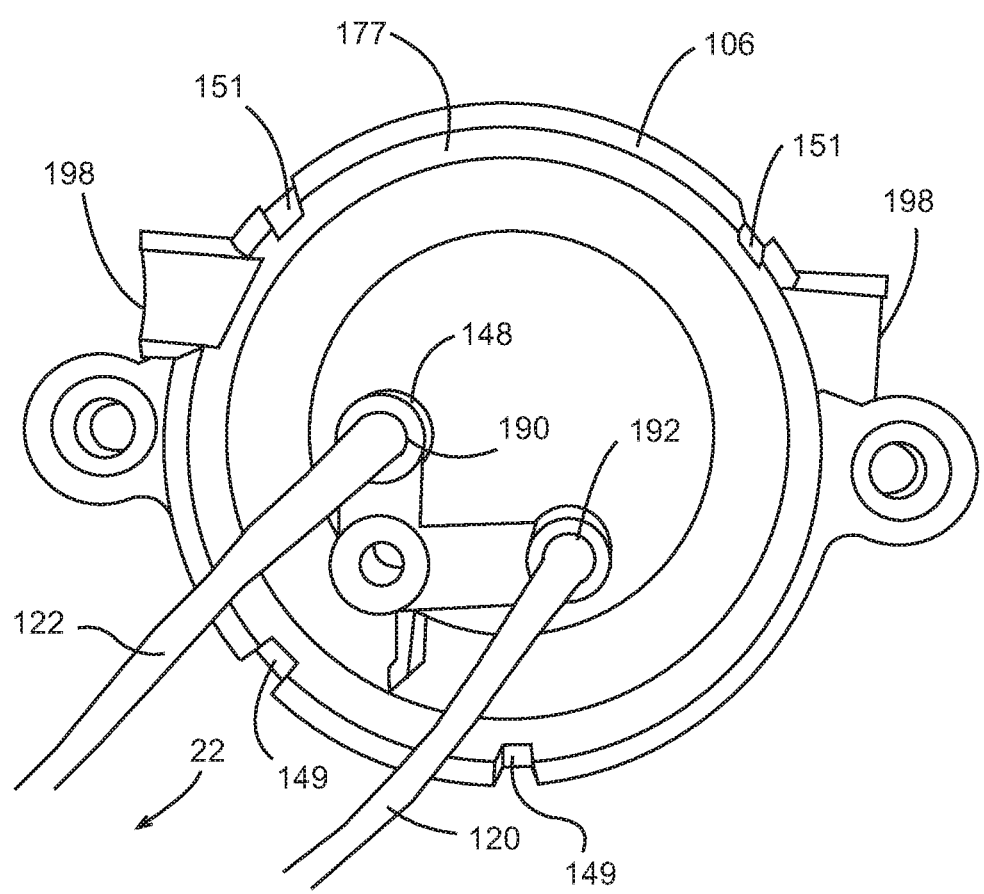
FIG. 13 is a bottom plan view of an electrode and ioniser shroud of the portable ozone generator depicted in FIG. 1.

Referring to FIGS. 10 and 12, support structure 58, which may include a plurality of plates 58A and 58B as shown, may comprise first surface 90, facing plate 34, and second surface 92, facing plate 36, opposed to one another and forming top and bottom surfaces in the example shown. Referring to FIG. 18, support structure 58 may define apertures 56 for one of a plurality of columns 54 to pass through, and in some cases structure 58 does not contact columns 54. Referring to FIGS. 10 and 12, support structure 58 may define an opening forming part of the air channel, for example a sleeve 74 for mounting fan 18. As illustrated in FIGS. 9 and 10, fan sleeve 74 may provide a seat for fan 18 when secured by suitable means of attachment, such as screws 80 (FIG. 9) and screw threads 82 (FIG. 10). Referring to FIG. 9, support structure 58 may comprise an interior partition wall 78 to divide the interior space of the perimeter side wall into first and second sections 86 and 88 respectively, each section forming an internal compartment. Referring to FIGS. 9 and 11, the first or second section may comprise fan 18 and a shroud 106 and the other of the first or second sections may comprise the battery 14, ozone generator 16, circuit board 20 and ioniser 22. Referring to FIGS. 9, 10, 11 and 12, support structure 58 may also define a wire passage opening 84 for wire access between the first surface 90 and the second surface 92. Referring to FIGS. 11 and 12, first surface 90 may define a recessed area or groove 98 configured for receiving a device for ozone output, such as a corona discharge tube 100. Referring to FIG. 13, shroud 106 may carry corresponding grooves 198 for cooperating with grooves 98 to mount tube 100 between the shroud 106 and surface 90. Referring to FIG. 12, surface 90 may also comprise screw receiving threads 102, 103, 104 and 105 for securing ozone generator 16, control board 20, ioniser 22, and shroud 106, respectively, to component support structure 58.

Referring to FIG. 8, housing 12 may mount one or more control buttons, 42 and 44, accessible from an exterior of the housing. For example, face plate 34 is shown defining openings 91 for buttons 42 and 44. Buttons 42 and 44 may be connected to relay control signals to the controller, for example circuit board 20, for example using depressible contacts 94 below buttons 42, 44. Buttons 42, 44 may be used to operate any one or more of the operating features of the device, for example the ability to turn on/off the function of the ozone generator 16 or ioniser 22, or to operate either function for a predetermined period of time as discussed below. Face plate 34 may define openings for a plurality of indicator lights 40, mounted on circuit board 20. Indicator lights may be used to provide operating or status information to the user, for example to convey an on status, a battery power level status, or to differentiate between the operation of the ioniser and ozone generator.

Referring to FIG. 11, battery 14 may be a permanent internal rechargeable battery, for example a Li-ion battery. Battery 14 may be wired to the circuit board 20 by positive and negative wires 112 and 114. The battery power output may be 5000 mAh, for example as supplied by dual Li-ion power cells, but is not limited to this value. The battery 14 may be selected to provide power for operation over a predetermined span of time, such as 8 or more hours. In a preferred embodiment, the rechargeable battery 14 is connected to be charged via power inlet 30 through circuit board 20. Battery 14 may also be used to power USB power outlet 28 via circuit board 20. Power and control connections between components may be achieved by wiring all components to circuit board 20 (shown), or by wiring components directly together (not shown).

Referring to FIGS. 9 and 11, ozone generator 16 (below the board 20 in FIG. 11, for example mounted on posts 103 in FIG. 12) may include a power converter or control box 170 (FIG. 9) and a corona discharge tube 100 (FIG. 100). Box 170 may be connected to receive power from battery 14 via control board 20 and wires 121 and 123. Referring to FIGS. 9 and 12, in one embodiment, ozone generator 16 may be secured to surface 90 by a suitable means of fastening, such as screws 172. Referring to FIG. 11, box 170 (FIG. 9) may be connected to a suitable output mechanism, such as a corona discharge tube 100, for example formed by connecting electrodes 200, 202 of tube 100 to input wires 174, 176. Referring to FIGS. 11 and 17, corona discharge tube 100 may facilitate the production of ozone through electric potential between exterior coiled electrode 200 and interior coiled electrode 202 across a dielectric tube 204, for example a quartz tube, and sufficient voltage supplied by ozone generator 16. Subsequent passage of a suitable fluid through air channel 110, such as oxygen, results in the production of ozone. Ozone generator 16 may be configured to output ozone at a non-zero rate that is at least 20 mg/hour and at most 50 mg/hour, for example between 20 and 30 mg/hour. Thus, ozone may be generated at a low rate, for example for a predetermined interval of time, such as 0-120 minutes or more, such as 30 or 60 minutes, selected by the user, for example using control buttons 42, 44. Plural time intervals may be pre-programmed and selectable, for example by selecting different buttons on the unit, each button being dedicated to a particular time interval, and/or a mechanism may be provided for manual entry of a specific time interval. The time interval and ozone release levels may be selected such that the external levels of ozone will not reach unsafe levels, for example 150 mg/L of ozone, or even levels that are 500, 1000, 5000, or more times lower than unsafe levels, during use of the device in a small unventilated room (for example 1 cubic meter). In some cases, unsafe levels will not be reached even in an unventilated bag (for example 1 L or smaller, for example a 133 mL space).

Referring to FIG. 17, in one embodiment, fan 18, shroud 106 and fan sleeve 74 may define air channel 110. As shown, air channel 110 may have a generally cylindrical cross-sectional shape from the air inlet 24 to the air outlet 26, with or without changes in internal diameter across air channel axis 130. Air inlet 24, air outlet 26, and air channel 110 may align to form a straight air flow path 128 into and out of housing 12, to reduce energy loss from friction and turbulence caused by circuitous flow paths. Fan 18 may be mounted within air channel 110 such that an axis of blade rotation 131 of blades 180 of fan 18 is parallel with air channel axis 130. Fan 18 may be a brushless DC fan, configured for silent operation to reduce noise production of generator 10. Axis 131 may be defined by a central hub 183 of fan 18. Hub 183 may be mounted to spin on one or more bearings (not shown). In one embodiment, partition plate 139 defines part of air channel 110 and mounts corona discharge tube 100 across air channel 110. Encircling wall 38 may comprise one or more lateral air inlets 32 communicating with air channel 110. Lateral side air vents or inlets 32 may provide air flow if air inlet 24 is blocked or restricted during operation. Air channel 110 ensures efficient fluid movement from air inlet 24 and side air inlets 32 past the corona discharge tube 100, to air outlet 26. Referring to FIG. 11, shroud 106 may be secured to surface 92 through screws 107.

Referring to FIG. 11, as stated circuit board 20 may be wired via wires 112, 114 to a suitable power source, such as battery 14, by a suitable connection such as soldering. Referring to FIGS. 9 and 11, circuit board 20 may also be wired to fan 18 by wired connections 116 and 118, for example through opening 84, to control the turn the fan on/off. Referring to FIG. 11 circuit board 20 may be wired to ioniser 22 by wired connections 124 and 126, to control the turn the ioniser on/off. Circuit board 20 may mount a timer to control the operation of all components on a timer. Circuit board 20 may be programmed to operate ozone generator 16 and/or ioniser 22 for a selected period of time in response to control signals to circuit board 20 from one or more control buttons 42, 44.

Referring to FIG. 11, air ioniser (or negative ion generator or "Chizhevsky's chandelier") may be a device that uses high voltage to ionise (electrically charge) air molecules. Negative ions, or anions, are particles with one or more extra electrons, conferring a net negative charge to the particle. Cations are positive ions missing one or more electrons, resulting in a net positive charge. Most commercial air purifiers are designed to generate negative ions. Another type of air ioniser is the ESD ioniser (balanced ion generator) used to neutralise static charge. Ionisers should not be confused with ozone generators, even though both devices operate in a similar way. Ionisers use electrostatically charged plates, such as electrodes 190, 192, to produce positively or negatively charged gas ions (for instance $N_2^-$ or $O_2^-$) that particulate matter sticks to in an effect similar to static electricity. Referring to FIGS. 11 and 13, ioniser 22 output may be wired to shroud 106 via wires 120 and 122. Referring to FIG. 13 shroud 106 may comprise sleeve 177 with slots 149 for entry of ioniser output wires 120 and 122, and slots 151 for entry of ozone generator wires 174, 176, into sleeve 177. Ioniser output may be within a suitable non-zero rate, such as $2-3 \times 10^{6}$ pcs/cm3 or above or below such a range.

A sensor (not shown) may be present to detect predetermined levels, such as unsafe levels, or levels that are 500, 1000, 5000, 10000, or more times lower than unsafe levels, of ozone in the external air, and the sensor may be connected to a controller that on detection of a predetermined external level of ozone operates to shut off the device. In some cases one or more of a timer, an ozone sensor, or another suitable mechanism is provided and programmed to control how long the ozone generator remains active and when the generator is turned off.

Referring to FIG. 16, a method of use of portable ozone generator 10 is shown. The method may include operating the circuit board 20 to instruct the ozone generator 16 to enter an ozone production mode by pressing buttons 42 or 44. Another method of use may include turning on the generator in an environment, with a controller provided to automatically shut off the unit based on certain characteristics such as the expiry of a predetermined time interval or the detection of a predetermined external ozone concentration. A further method of use may include deodorizing one or more items, for example fabric or material such as towel 132, by placing the hand-held portable ozone generator 10, while in the ozone production mode, in a bag 134 along with the one or more items. The device may be used to remove smells from items, such as hockey or other sports equipment, or smells in a small room. Ozone generator 10 may be connected to a USB-powered device, such as phone 136, for charging purposes while ozone production mode is on or off. The bag 134 may be sealed, for example using a ZIPLOCK™ closure mechanism. The generator 10 may be used in other applications, such as deodorizing footwear, clothing, and rooms. The generator 10 may be used to kill bacteria and sterilize items.

Figure 20:
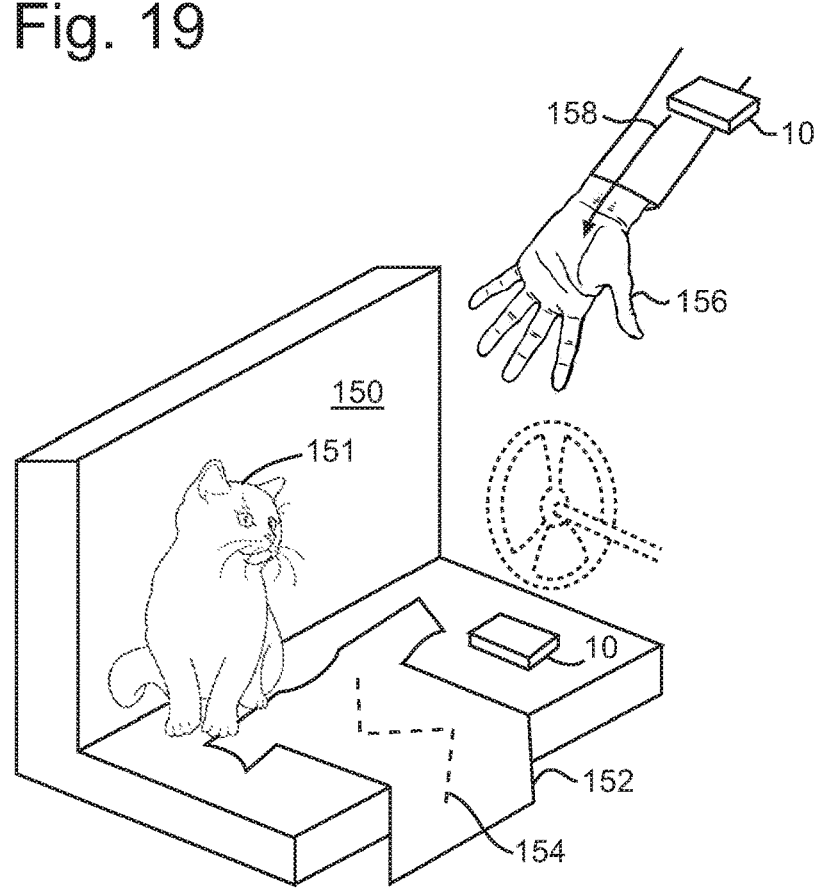
FIG. 20 is a perspective view of a portable ozone generator in use within an enclosed area such as a vehicle.

Referring to FIG. 20, an example of a method of use of portable ozone generator 10 is depicted. Ozone generator 10 may be used to deodorize an area 150, such as the interior of a vehicle or an area that contains odor from one or more pets 151. Other examples of area 150 include the interior of a recreational vehicle, or a room in a hunting lodge or house. Ozone generator 10 may be also used to deodorize clothing 152, such as scent resistant clothing, clothing imbued with activated carbon or silver, hunting clothes or sports clothes. Deodorizing may be achieved by exposing the clothes 152 or equipment to ozone via an ozone stream 154 or by direct contact of clothing 152/equipment with generator 10 with or without the use of a bag to contain the clothing/equipment and generator. Ozone generator 10 may be used to deodorize a user's body 156 or clothing. The user may place ozone generator 10 in direct contact with the user's skin or clothing worn by the user, and may apply ozone to the contact surface by leaving the generator 10 in place or by rubbing or directing the generator 10 along the surface of the skin or clothing, for example along the path of the direction arrow 158.

The term hand-held may refer to a device that has external dimensions sized to fit within a user's hand, for example an average adult male or female's hand, and with a weight sufficiently small to be conveniently operated by a user. Hand-held may also refer to a device that can fit in a person's hand while being operated by the same hand. The housing 12 may be sized such that one of the plates 34, 36 may be positioned in the palm of a user's hand, and the thumb tip and finger tips of the user can extend simultaneously around opposed sides of the device to reach and access the other plate 34, 36. A maximum length of the device may be commensurate with or shorter than a length from the base of the user's palm to the middle finger tip. In one case the respective individual surface areas of the external facing side of the face plate 34, 36, or both, are commensurate with or smaller than the surface area of a user's palm. The generator 10 may have a ratio of thickness of the encircling wall 38 between plates 34, 36: a local maximum external dimension (such as width) of the face plate 34, 36, or both, that is less than 1:2. The generator 10 may have a ratio of thickness of the encircling wall 38 between plates 34, 36: the maximum external dimension (such as length) of the face plate 34, 36, or both, that is less than 1:3. In one case the device is approximately the same size and shape as a cellular phone such as the IPHONE™ 6S™ or a large size 25 cigarette package commonly sold in Canada. Hence, the device may be readily carried in one's pocket or purse without causing the user any significant inconvenience.

The devices (portable ozone generator 10) disclosed here, or parts of the device, may be made by suitable material, for example ABS plastic for the housing 12. The housing 12 may be sufficiently rigid to permit a vehicle to drive over top of the housing 12 without reducing functionality of the device. The device may be remotely operated, for example using an application on a cell phone or wall mounted device to access and control the device through a wired connection or a wireless connection such as wifi or BLUETOOTH™. Permanent battery install may refer to a battery that cannot be removed from the unit without damaging the unit, or without removing fasteners such as screws. Wherever screws are disclosed, other suitable fasteners may be used such as bolts, nuts, adhesives, welding, soldering, and others. Power input and/or power output may be a suitable voltage and amperage, such as 5V and 1 A. Ozone rates may be above 50 mg/hour. The controller may form part of the ozone generator. A controller includes a printed circuit board assembly as shown, although other controllers may be used such as a programmable logic controller. In one case the controller includes an electrical switch for completing a circuit to supply power to the ozone generator. The device may be provided as an add-on component for a tablet or other computing device such as an IPAD™ or phone. Parts of either plate 34, 36 may be formed on the other plate 34, 36. The controller may be programmable, for example to enter user-selected periods of operation. One button 42 may provide 1 hour of ozone operation, the other button 44 may provide 3 hours of ozone operation. Referring to FIG. 8, one or more rings 193 may be fitted around outlet 26, or inlet 24 in one case.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follows:

1. A hand-held portable ozone generator comprising:
   a housing defining an air inlet, an air outlet, and an air channel communicating between the air inlet and the air outlet, in which the housing comprises an encircling wall and first and second face plates opposing one another, with external surfaces of the housing forming a plank shape, the air channel being defined within the housing by a shroud and a sleeve such that the air channel is distinct from an interior of the housing;
   a fan mounted across the air channel such that an axis of blade rotation of the fan is parallel with an air channel axis of the air channel, in which the air inlet is defined through the first face plate, the air outlet is defined through the second face plate; and the air inlet, air outlet, and air channel align to form a straight air flow path, which is perpendicular to the first face plate and the second face plate, into the housing, through the fan, and out of the housing;
   a battery;
   an ozone generator configured to output, during operation, ozone into the air channel at a non-zero rate that is equal to or below 50 mg/hour; and
   a controller connected to send control signals to the ozone generator in response to user input.

2. The hand-held portable ozone generator of claim 1 in which the ozone generator is configured to output ozone at a non-zero rate that is at least 20 mg/hour and at most 50 mg/hour.

3. The hand-held portable ozone generator of claim 1 in which the encircling wall comprises one or more lateral air inlets communicating with the air channel.

4. The hand-held portable ozone generator of claim 1 in which:
   the first face plate is shaped to permit air flow into the air inlet when the first face plate is resting on a planar surface; and
   the second face plate is shaped to permit air flow into the air outlet when the second face plate is resting on the planar surface.

5. The hand-held portable ozone generator of claim 1 in which the air channel has a generally cylindrical cross-sectional shape from the air inlet to the air outlet.

6. The hand-held portable ozone generator of claim 1 in which the encircling wall defines a support structure laterally extended between opposed interior facing surfaces of the encircling wall, the support structure located part way between the first and second face plates, the support structure mounting the battery, ozone generator, and controller.

7. The hand-held portable ozone generator of claim 6 in which the support structure comprises a partition plate that defines part of the air channel and mounts a corona discharge electrode, of the ozone generator, across the air channel.

8. The hand-held portable ozone generator of claim 6 further comprising plural reinforcing members extended internally between the first and second face plates.

9. The hand-held portable ozone generator of claim 8 in which the plural reinforcing members comprise posts that pass through apertures defined in the support structure.

10. The hand-held portable ozone generator of claim 8 in which the battery forms a reinforcing member extended between the first and second face plates.

11. The hand-held portable ozone generator of claim 1 further comprising one or more control buttons accessible from an exterior of the housing, and the controller is programmed to operate the ozone generator for a selected period of time in response to control signals to the controller from the one or more control buttons.

12. The hand-held portable ozone generator of claim 1 in which the battery is a permanent internal rechargeable battery.

13. The hand-held portable ozone generator of claim 1 further comprising a USB power output connected to the battery and accessible from an exterior of the housing.

14. The hand-held portable ozone generator of claim 1 further comprising operating the controller to instruct the ozone generator to enter an ozone production mode.

15. The hand-held portable ozone generator of claim 14 further comprising deodorizing one or more items by placing the hand-held portable ozone generator, while in the ozone production mode, in a bag along with the one or more items.

* * * * *